US008652059B2

(12) United States Patent
Sano et al.

(10) Patent No.: US 8,652,059 B2
(45) Date of Patent: Feb. 18, 2014

(54) CUFF FOR BLOOD PRESSURE INFORMATION MEASUREMENT DEVICE AND BLOOD PRESSURE INFORMATION MEASUREMENT DEVICE PROVIDED WITH THE SAME

(75) Inventors: Yoshihiko Sano, Kyoto (JP); Chisato Uesaka, Kyoto (JP); Bo Zhao, Dalian (CN)

(73) Assignee: OMRON HEALTHCARE Co., Ltd., Kyoto (JP)

(*) Notice: Subject to any disclaimer, the term of this patent is extended or adjusted under 35 U.S.C. 154(b) by 400 days.

(21) Appl. No.: 13/030,857

(22) Filed: Feb. 18, 2011

(65) Prior Publication Data
US 2011/0144507 A1    Jun. 16, 2011

Related U.S. Application Data

(63) Continuation of application No. PCT/JP2009/063854, filed on Aug. 5, 2009.

(30) Foreign Application Priority Data

Aug. 22, 2008 (JP) ................................. 2008-214251

(51) Int. Cl.
*A61B 5/02* (2006.01)
(52) U.S. Cl.
USPC ........................................................ 600/499
(58) Field of Classification Search
USPC .......... 600/485, 490, 491, 493, 499; 606/201, 606/202, 203
See application file for complete search history.

(56) References Cited

U.S. PATENT DOCUMENTS

| 2005/0131310 A1* | 6/2005 | Freund et al. ................. 600/499 |
| 2006/0047206 A1* | 3/2006 | Sano et al. ..................... 600/490 |

(Continued)

FOREIGN PATENT DOCUMENTS

| JP | 52-18515 | 2/1977 |
| JP | 61-238229 | 10/1986 |

(Continued)

OTHER PUBLICATIONS

International Search Report for Internation Application No. PCT/JP2009/063854, mailed on Aug. 26, 2009 (4 pages).

(Continued)

*Primary Examiner* — Navin Natnithithadha
*Assistant Examiner* — Etsub Berhanu
(74) *Attorney, Agent, or Firm* — Osha Liang LLP

(57) ABSTRACT

A cuff includes a cuff main body portion and a gripping portion provided on an outer peripheral surface of the cuff main body portion. The cuff main body portion includes an air bladder, a tightening belt wrapped around an outer side of the air bladder, and a wrapping length adjustment mechanism for variably adjusting a wrapping length of the tightening belt. The wrapping length adjustment mechanism has a bias spring for pulling and biasing the tightening belt in a direction in which the wrapping length of the tightening belt is shortened, a first restriction portion for restricting extension of the wrapping length, and a second restriction portion for restricting shortening of the wrapping length. The gripping portion includes a push button for switching actions of the two restriction portions. In this configuration, the cuff may be easily attached to a measurement site regardless of the circumferential length of the site.

6 Claims, 11 Drawing Sheets

(56) References Cited

U.S. PATENT DOCUMENTS

| | | |
|---|---|---|
| 2008/0132795 A1 | 6/2008 | Ghigini |
| 2011/0009757 A1* | 1/2011 | Sano et al. .................... 600/499 |
| 2011/0112412 A1* | 5/2011 | Sano et al. .................... 600/499 |

FOREIGN PATENT DOCUMENTS

| | | |
|---|---|---|
| JP | 3-126102 | 5/1991 |
| JP | 2002-209858 A | 7/2002 |
| JP | 2006-68318 | 3/2006 |
| JP | 2007-75294 | 3/2007 |
| JP | 3139024 | 1/2008 |
| JP | 2008-528151 | 7/2008 |
| JP | 2009225855 A * | 10/2009 |
| WO | 03/101290 A2 | 12/2003 |

OTHER PUBLICATIONS

Patent Abstracts of Japan for Japanese Publication No. 2007-075294, Publication date Mar. 29, 2007 (1 page).

Patent Abstracts of Japan for Japanese Publication No. 2006-068318, Publication date Mar. 16, 2006 (1 page).

Patent Abstracts of Japan for Japanese Publication No. 2002-209858, Publication date Jul. 30, 2002 (1 page).

Patent Abstract for Japanese registered utility model No. 3139024, Registration date Jan. 9, 2008 (1 page).

Patent Abstracts of Japan for Japanese Publication No. 03-126102, Publication date May 29, 1991 (1 page).

Patent Abstracts of Japan for Japanese Publication No. 52-018515, Publication date Feb. 12, 1977 (1 page).

* cited by examiner

CUFF FOR BLOOD PRESSURE INFORMATION MEASUREMENT DEVICE AND BLOOD PRESSURE INFORMATION MEASUREMENT DEVICE PROVIDED WITH THE SAME

TECHNICAL FIELD

The present invention relates to a blood pressure information measurement device capable of measuring blood pressure information such as blood pressure values, and a cuff for a blood pressure information measurement device provided in the same.

BACKGROUND ART

It is highly important to acquire blood pressure information of a subject for knowing a health condition of the subject. In recent years, there have been attempts to capture changes in a cardiac load and hardness of an artery not only by acquiring a systolic blood pressure value (a maximal blood pressure value), a diastolic blood pressure value (a minimal blood pressure value), and the like, which are conventionally widely recognized as useful representative indicators for health management, but also by acquiring a pulse wave of the subject. A blood pressure information measurement device is a device for obtaining these indicators for health management based on the acquired blood pressure information, and such a device is expected to be further utilized in fields of early detection, prevention, and treatment of circulatory diseases, and the like. It should be noted that the blood pressure information widely includes various information relating to a circulatory system such as the systolic blood pressure value, the diastolic blood pressure value, an average blood pressure value, the pulse wave, pulsation, and an AI (Augmentation Index) value.

In general, a cuff accommodating a fluid bag is utilized for measurement of the blood pressure information. The cuff is a band-shaped structure having an inner cavity that is capable of being wound around part of a living body, the cuff being utilized for the measurement of the blood pressure information by infusing a fluid such as gas and a liquid into the inner cavity so as to expand and contract the fluid bag. For example, in the blood pressure information measurement device (hereinafter, also simply referred to as a sphygmomanometer) for measuring the blood pressure values such as the systolic blood pressure value and the diastolic blood pressure value, the cuff accommodating the fluid bag for compressing the artery is wound around a body surface of the living body, and the wound fluid bag is expanded and contracted, so that an arterial blood pressure pulse wave is captured as a change in inner pressure of the fluid bag. Thus, the blood pressure values are measured. It should be noted that a cuff particularly wound around an arm and used in this way is also called an arm band or a manchette.

In the cuff, there is a need for reliably winding a cuff main body portion to be attached to a measurement site around the living body so as to reliably fix the fluid bag to the measurement site of the living body. However, in a general cuff, because a winding task is left to the hands of the subject, reliable winding is not always reproduced. In a case where the reliable winding is not reproduced, measurement values are varied, making it difficult to precisely and stably measure the blood pressure information.

Thus, variously formed cuffs have been conventionally proposed for reliably winding the cuff around the measurement site with favorable reproducibility. For example, Japanese Unexamined Patent Publication No. S61-238229 (Patent Document 1), Japanese Unexamined Patent Publication No. 2002-209858 (Patent Document 2), and the like disclose a cuff accommodating a curved elastic plate called a curler inside in addition to an air bladder serving as the fluid bag. The curler is accommodated inside the cuff for maintaining an annular form of the cuff. The curler is annularly wrapped around an outer side of the air bladder and arranged inside the cuff, so that the cuff is formed to be elastically deformable in a radial direction. In the cuff provided with such a curler, the air bladder is fixed while being pushed toward the measurement site by the curler with proper pressing force after attachment. Thus, reliable fixation of the air bladder to the measurement site is reproduced.

However, in the cuff accommodating the above curler, the curler is shaped so that the curler at the time of non-attachment has a more reduced diameter than the measurement site in order to reliably press the air bladder onto the measurement site at the time of attaching the cuff. As such, the curler in a reduced diameter state is required to be once pushed and extended before attachment to the measurement site.

In order to further easily attach the cuff accommodating the above curler, Japanese Unexamined Patent Publication No. 2006-68318 (Patent Document 3) discloses a configuration of a cuff attachable to and detachable from the measurement site with a single touch operation. In the cuff disclosed in Japanese Unexamined Patent Publication No. 2006-68318, an elastic member such as a bias spring and a power transmission mechanism such as a slider are built inside the cuff, so that the cuff is attached to the measurement site with favorable reproducibility by a bias force of the bias spring with an optimal tightening force, and the size of the cuff including the curler in the radial direction is variable in conjunction with the operation of a user. Thereby, the cuff can be attached and detached with the single touch operation.

Japanese Unexamined Patent Publication No. 2007-75294 (Patent Document 4) and International Publication WO 03/101290 (Patent Document 5) disclose a cuff in which a winding device including a bias spring and a winding roller is built inside the cuff, and one end of a band-shaped belt member to which an air bladder is attached is wound by the winding device, so that the cuff is attached to the measurement site with favorable reproducibility by a bias force of the bias spring with optimal tightening force.

Patent Document 1: Japanese Unexamined Patent Publication No. S61-238229
Patent Document 2: Japanese Unexamined Patent Publication No. 2002-209858
Patent Document 3: Japanese Unexamined Patent Publication No. 2006-68318
Patent Document 4: Japanese Unexamined Patent Publication No. 2007-75294
Patent Document 5: International Publication WO 03/101290

However, in the cuff disclosed in Japanese Unexamined Patent Publication No. 2007-75294 and International Publication WO 03/101290, the cuff in the non-attachment state has a non-annular form. Thus, there is a need for fixing the cuff to the measurement site in a state that the cuff is annularly wrapped around the measurement site, so that engagement portions for engagement are provided in one end and another end of the band-shaped belt member. In a case of the cuff with such a configuration, there is a need for engaging the engagement portions while maintaining a state that the band-shaped belt member is placed on the measurement site during attachment. Thus, because it is difficult to perform the operation with a single hand, the operation is forced to be performed with both hands. Therefore, in a case where the cuff with the above configuration is adopted in a sphygmomanometer for a domestic use which requires the subject winding the cuff around one of his/her arms by himself/herself, there is a problem that the attachment of the cuff is not easily performed by himself/herself in the first place.

Meanwhile, in the cuff disclosed in Japanese Unexamined Patent Publication No. 2006-68318, the cuff has an annular form in the non-attachment state. Thus, by inserting the measurement site into a hollow opening portion thereof, the cuff can be attached and detached with a single touch operation of a single hand. However, for convenience of the configuration of the device, the size of the cuff including the curler in the radial direction cannot be varied without restriction, so there is a problem that applicable circumferential length of the measurement site is restricted.

Therefore, one or more embodiments of the present invention provides a cuff for a blood pressure information measurement device capable of being easily attached to a measurement site of a living body in which applicable circumferential length of the measurement site is not restricted, and a blood pressure information measurement device provided with the same.

SUMMARY OF THE INVENTION

One or more embodiments of the present invention provides a cuff for a blood pressure information measurement device attached to a measurement site of a living body and used for measurement of blood pressure information, including a cuff main body portion, a gripping portion, and a switching portion. The cuff main body portion is formed into an annular form into which the measurement site is insertable from an axial direction and attached to the measurement site at the time of measurement. The gripping portion is provided on an outer peripheral surface of the cuff main body portion. The cuff main body portion includes a fluid bag for compressing the living body, a tightening belt wrapped around an outer side of the fluid bag, and a wrapping length adjustment mechanism for variably adjusting a wrapping length of the tightening belt. The wrapping length adjustment mechanism has a bias portion for pulling and biasing the tightening belt in a direction in which the wrapping length of the tightening belt is shortened, a first restriction portion for restricting extension of the wrapping length of the tightening belt, and a second restriction portion for restricting shortening of the wrapping length of the tightening belt. The switching portion selectively switches whether the wrapping length adjustment mechanism is in a first state where restriction by the second restriction portion is released, restriction by the first restriction portion is applied, and thereby, the wrapping length of the tightening belt is variably adjusted only in the direction in which the tightening belt is pulled by the bias portion and the wrapping length thereof is shortened, or in a second state where the restriction by the first restriction portion is released, the restriction by the second restriction portion is applied, and thereby, the wrapping length of the tightening belt is variably adjustable only in the direction in which the wrapping length of the tightening belt is extended. The switching portion is provided in the gripping portion or the cuff main body portion in the vicinity of the gripping portion.

In the cuff for a blood pressure information measurement device according to one or more embodiments of the present invention, the switching portion is preferably formed by a push button. In this case, preferably, the wrapping length adjustment mechanism is in the second state in conjunction with a press-down state of the push button, and in the first state in conjunction with release of the press-down state of the push button.

In the cuff for a blood pressure information measurement device according to one or more embodiments of the present invention, the wrapping length adjustment mechanism preferably includes a winding roller capable of winding and feeding the tightening belt. In such a case, the bias portion is preferably formed by a spring attached to the winding roller. In such a case, each of the first restriction portion and the second restriction portion is preferably formed by a one-way clutch additionally provided in the winding roller.

The cuff for a blood pressure information measurement device according to one or more embodiments of the present invention further includes a flexible curved elastic plate elastically deformable in a radial direction of the cuff main body portion on the outer side of the fluid bag and on the inner side of the tightening belt.

A blood pressure information measurement device according to one or more embodiments of the present invention includes a cuff for a blood pressure information measurement device according to one or more embodiments of the present invention, expanding/contracting mechanisms for expanding and contracting a fluid bag, and a blood pressure information acquiring unit for acquiring blood pressure information.

One or more embodiments of the present invention provides a cuff for a blood pressure information measurement device capable of being easily attached to a measurement site of a living body in which an applicable circumferential length of the measurement site is not restricted, and a blood pressure information measurement device provided with the same.

DETAILED DESCRIPTION OF THE INVENTION

Embodiments of the present invention will be hereinafter described in detail with reference to the drawings. It should be noted that in the embodiments hereinafter, a sphygmomanometer cuff adapted to be wound around an upper arm and used, and a sphygmomanometer provided with the same will be shown as an example and described as a cuff for a blood pressure information measurement device, and a blood pressure information measurement device provided with the same.

Figure 1:
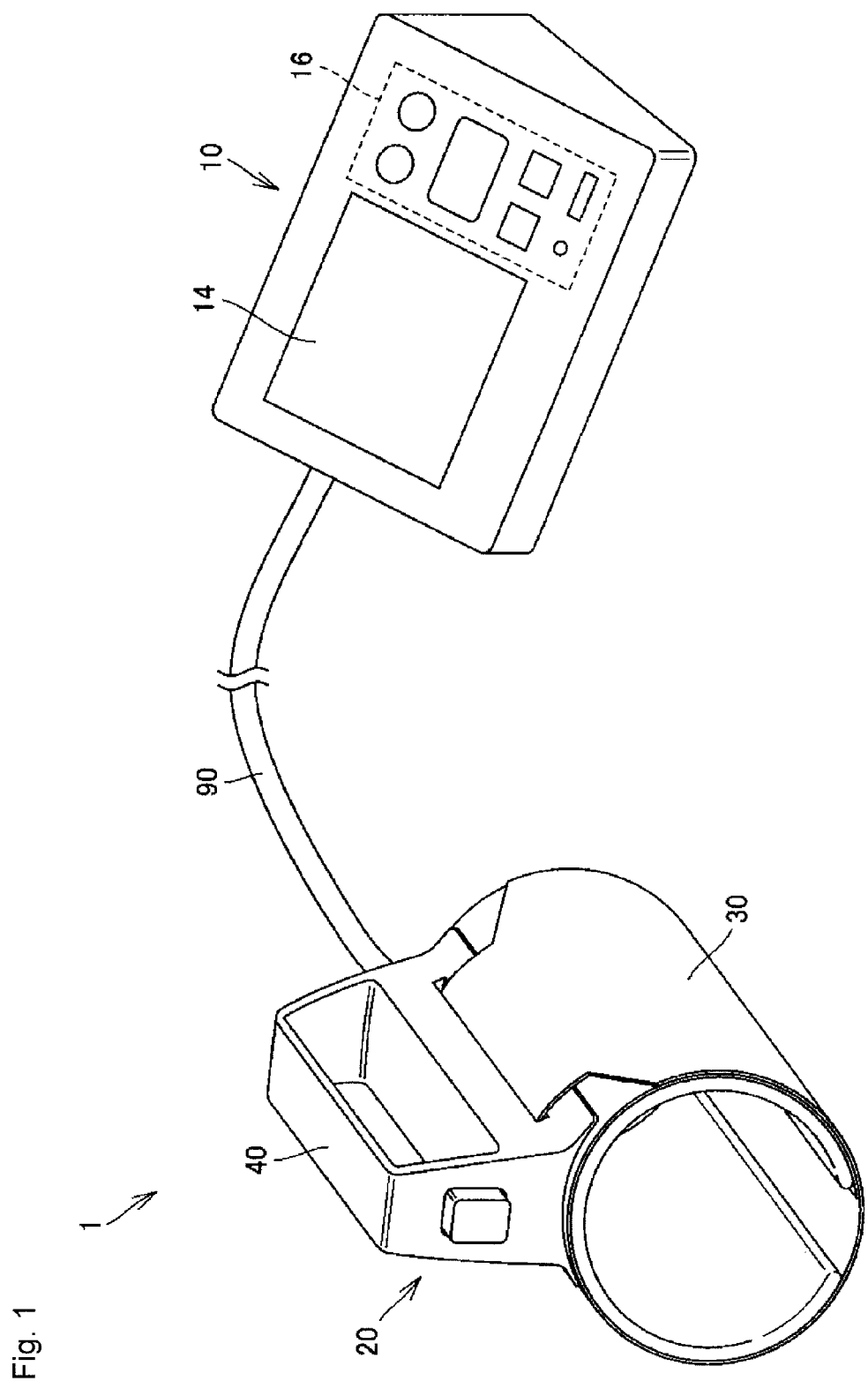
FIG. 1 is a perspective view showing an outer appearance structure of a sphygmomanometer in an embodiment of the present invention.
Figure 2:
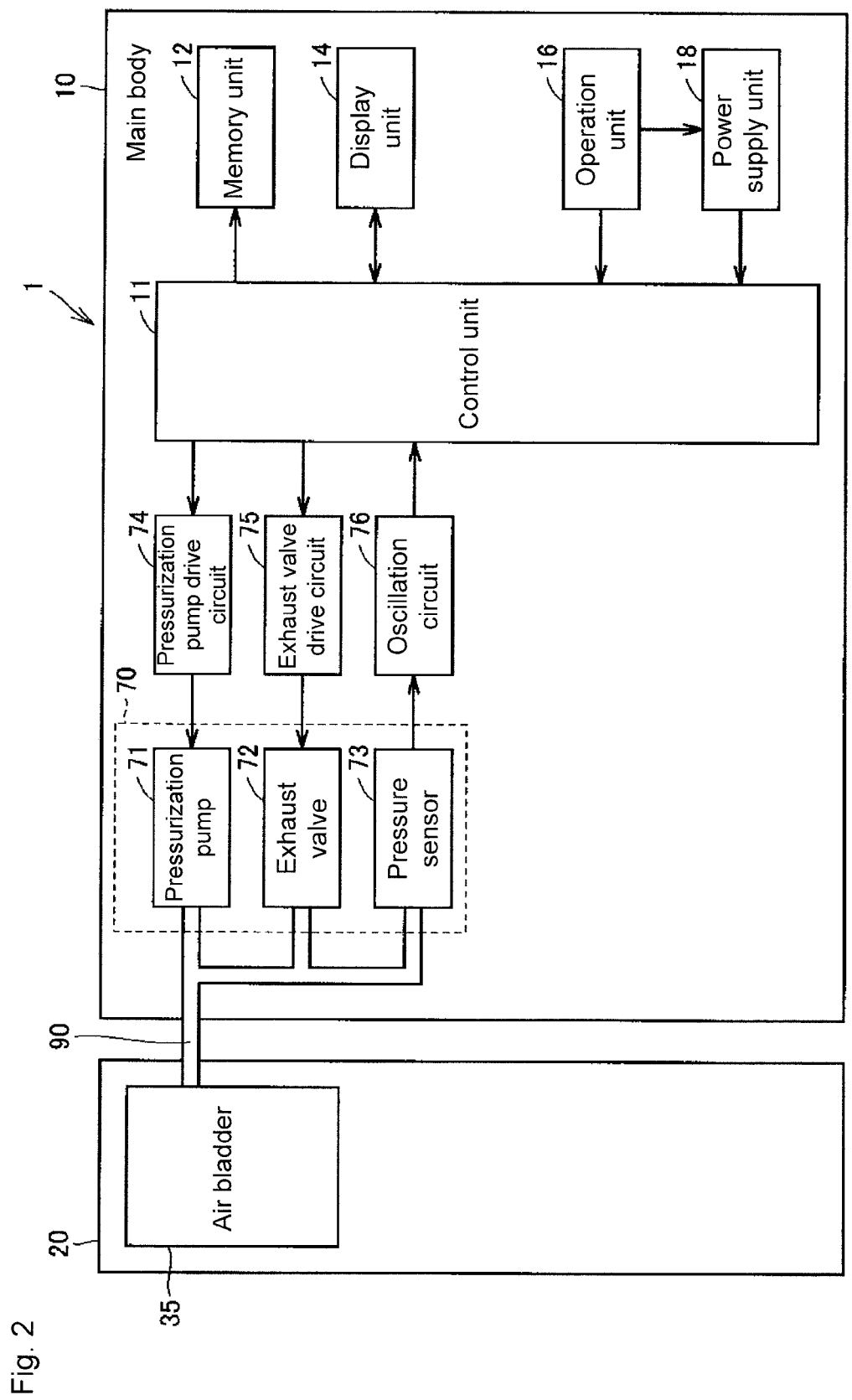
FIG. 2 is a functional block configuration diagram of the sphygmomanometer in an embodiment of the present invention.

FIG. 1 is a perspective view showing an outer appearance structure of a sphygmomanometer in an embodiment of the present invention, and FIG. 2 is a functional block configuration diagram of the sphygmomanometer shown in FIG. 1. Firstly, the outer appearance structure and the configuration of the sphygmomanometer in the present embodiment will be described with reference to FIGS. 1 and 2.

As shown in FIG. 1, a sphygmomanometer 1 in the present embodiment is provided with a main body 10, a cuff 20, and an air tube 90. The main body 10 has a box shape casing, and is provided with a display unit 14 and an operation unit 16 on an upper surface thereof. The main body 10 is mounted on a mount surface such as a table and used at the time of measurement. The cuff 20 has a tubular cuff main body portion 30 including a hollow opening portion into which the upper arm is insertable from the axial direction, and a gripping portion 40 provided on an outer peripheral surface of the cuff main body portion 30. The cuff 20 is attached to the upper arm and used at the time of the measurement. The air tube 90 connects the main body 10 and the cuff 20 which are separated from each other.

As shown in FIG. 2, the main body 10 has a control unit 11, a memory unit 12, a power supply unit 18, a pressurization pump 71, an exhaust valve 72, a pressure sensor 73, a pressurization pump drive circuit 74, an exhaust valve drive circuit 75, and an oscillation circuit 76 in addition to the above display unit 14 and the operation unit 16. Meanwhile, the cuff 20 mainly has an air bladder 35 serving as a fluid bag. The pressurization pump 71, the exhaust valve 72, and the pressure sensor 73 correspond to air system components 70 provided in the sphygmomanometer, and particularly, the pressurization pump 71 and the exhaust valve 72 correspond to expanding/contracting mechanisms for expanding and contracting the air bladder 35.

The air bladder 35 is the fluid bag for compressing the upper arm in an attachment state, and has expansion/contraction space serving as an inner cavity inside thereof. The air bladder 35 is respectively connected to the pressurization pump 71, the exhaust valve 72, and the pressure sensor 73, serving as the above air system components 70 via the above air tube 90.

The control unit 11 is formed by, for example, a CPU (Central Processing Unit), serving as a part for controlling the entire sphygmomanometer 1. The memory unit 12 is formed by, for example, a ROM (Read-Only Memory) and a RAM (Random-Access Memory), serving as a part for storing a program to have the control unit 11 and the like execute processing procedures for the measurement of blood pressure values, and storing measurement results and the like. The display unit 14 is formed by, for example, a LCD (Liquid Crystal Display), serving as a part for displaying the measurement results and the like. The operation unit 16 serves as a part for receiving operation by a subject or the like and inputting this command from the outside to the control unit 11 and the power supply unit 18. The power supply unit 18 serves as a part for supplying electric power as a power supply to the control unit 11.

The control unit 11 respectively inputs control signals for driving the pressurization pump 71 and the exhaust valve 72 to the pressurization pump drive circuit 74 and the exhaust valve drive circuit 75, and inputs the blood pressure values as the measurement results to the memory unit 12 and the display unit 14. The control unit 11 includes a blood pressure information acquiring unit (not shown) for acquiring the blood pressure values of the subject based on pressure values detected by the pressure sensor 73. The blood pressure values acquired by the blood pressure information measuring unit are inputted to the above memory unit 12 and the display unit 14 as the measurement results. It should be noted that the sphygmomanometer 1 may separately have an output unit for outputting the blood pressure values as the measurement results to external devices (such as a PC (Personal Computer) and a printer). For example, a serial communication line, a write device to various recording media, and the like can be utilized as the output unit.

The pressurization pump drive circuit 74 controls an action of the pressurization pump 71 based on the control signal inputted from the control unit 11. The exhaust valve drive circuit 75 controls an opening/closing action of the exhaust valve 72 based on the control signal inputted from the control unit 11. The pressurization pump 71 pressurizes the internal pressure of the air bladder 35 (hereinafter, also referred to as the "cuff pressure") by supplying the air into the inner cavity of the air bladder 35, and the action thereof is controlled by the above pressurization pump drive circuit 74. The exhaust valve 72 maintains the internal pressure of the air bladder 35 and reduces the cuff pressure by opening the inner cavity of the air bladder 35 to the outside, and the action thereof is controlled by the above exhaust valve drive circuit 75. The pressure sensor 73 inputs an output signal in accordance with the internal pressure of the air bladder 35 to the oscillation circuit 76. The oscillation circuit 76 generates a signal of an oscillating frequency in accordance with the signal inputted from the pressure sensor 73 and inputs the generated signal to the control unit 11.

Figure 3:
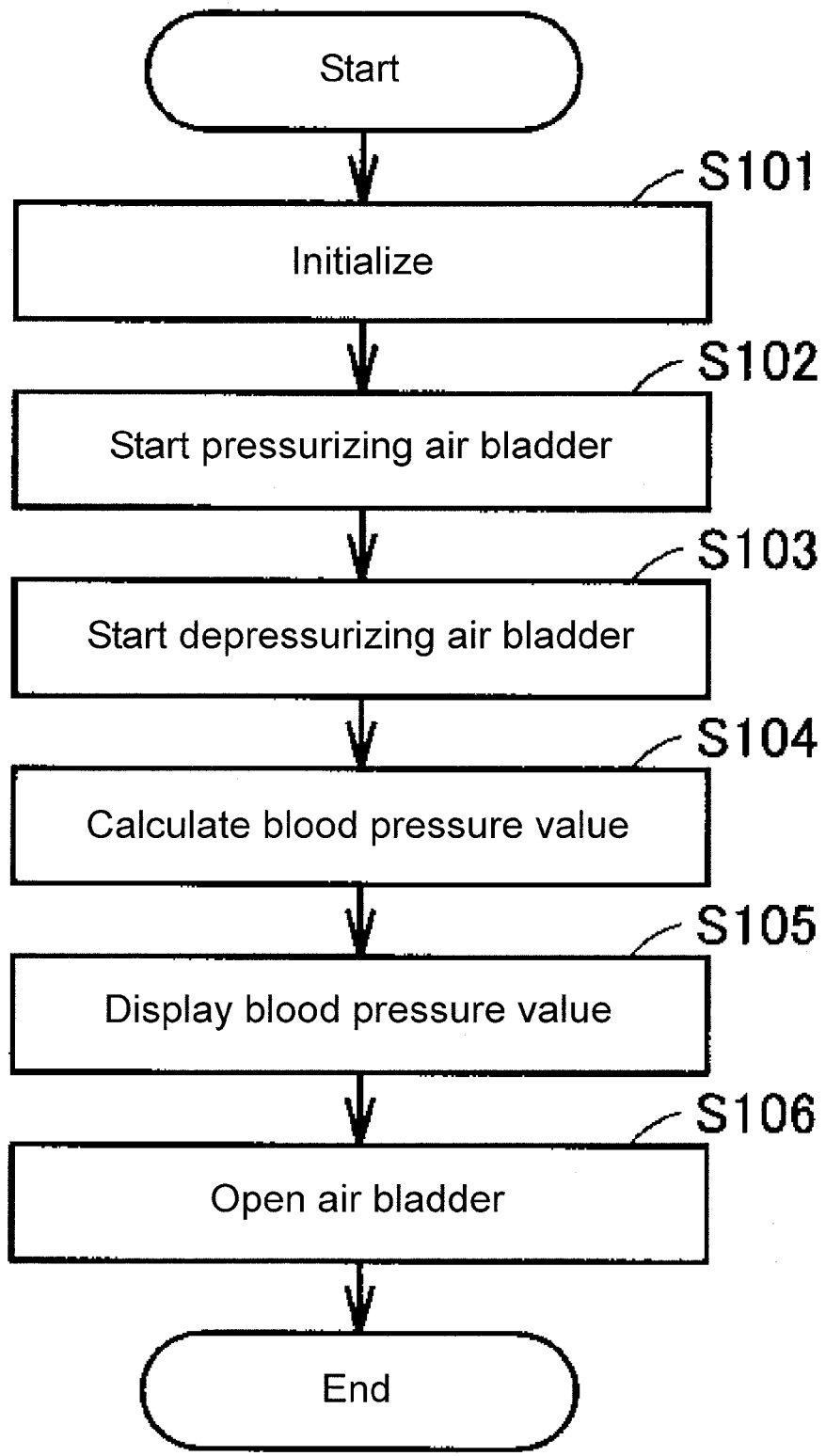
FIG. 3 is a flowchart showing a flow of measurement processing of blood pressure values of the sphygmomanometer in an embodiment of the present invention.

FIG. 3 is a flowchart showing a flow of measurement processing of the blood pressure values of the sphygmomanometer in the present embodiment. Next, the flow of the measurement processing of the blood pressure values of the sphygmomanometer in the present embodiment will be described with reference to FIG. 3. It should be noted that a program following the flowchart is preliminarily stored in the memory unit 12, and the control unit 11 reads out the program from the memory unit 12 and executes the program, so that processing thereof is executed.

When measuring the blood pressure values, the subject preliminarily attaches the cuff 20 to the upper arm, and operates the operation unit 16 provided in the main body 10 in this state so as to turn on the power supply of the sphygmomanometer 1. Thereby, the electric power as the power supply is supplied from the power supply unit 18 to the control unit 11, so that the control unit 11 is driven. As shown in FIG. 3, the control unit 11 firstly initializes the sphygmomanometer 1 after driving thereof (step S101).

Next, the control unit 11 waits for an instruction of measurement start of the subject. In a case where the subject operates the operation unit 16 so as to give the instruction of the measurement start, the control unit 11 closes the exhaust valve 72 and starts driving the pressurization pump 71 so as to gradually increase the cuff pressure of the air bladder 35 (step S102). In a process of gradually pressurizing the air bladder 35, when the cuff pressure reaches a predetermined level for the measurement of the blood pressure values, the control unit 11 stops the pressurization pump 71 and then gradually opens the closed exhaust valve 72 so as to gradually exhaust the air in the air bladder 35 and gradually reduce the cuff pressure (step S103). In the sphygmomanometer 1 in the present embodiment, the blood pressure values are measured in the slow depressurization process of the cuff pressure.

Next, the control unit 11 calculates the blood pressure values such as a systolic blood pressure value and a diastolic blood pressure value by a known procedure (step S104). Specifically, the control unit 11 extracts pulse wave information based on the oscillating frequency obtained from the oscillation circuit 76 in the process of gradually reducing the cuff pressure of the air bladder 35. Then, the control unit 11 calculates the blood pressure values based on the extracted pulse wave information. When the blood pressure values are calculated in step S104, the control unit 11 displays the blood pressure values as the measurement results on the display unit 14 (step S105) and stores the blood pressure values in the memory unit 12.

After that, the control unit 11 opens the air bladder 35 so as to completely exhaust the air in the air bladder 35 (step S106), waits for an instruction of power-off of the subject, and then finishes the action thereof. It should be noted that the measurement method described above is based on a so-called depressurization measurement method of detecting the pulse wave at the time of depressurization of the air bladder 35. However, a so-called pressurization measurement method of detecting the pulse wave at the time of pressurization of the air bladder 35 can be adopted as a matter of course.

Figure 4:
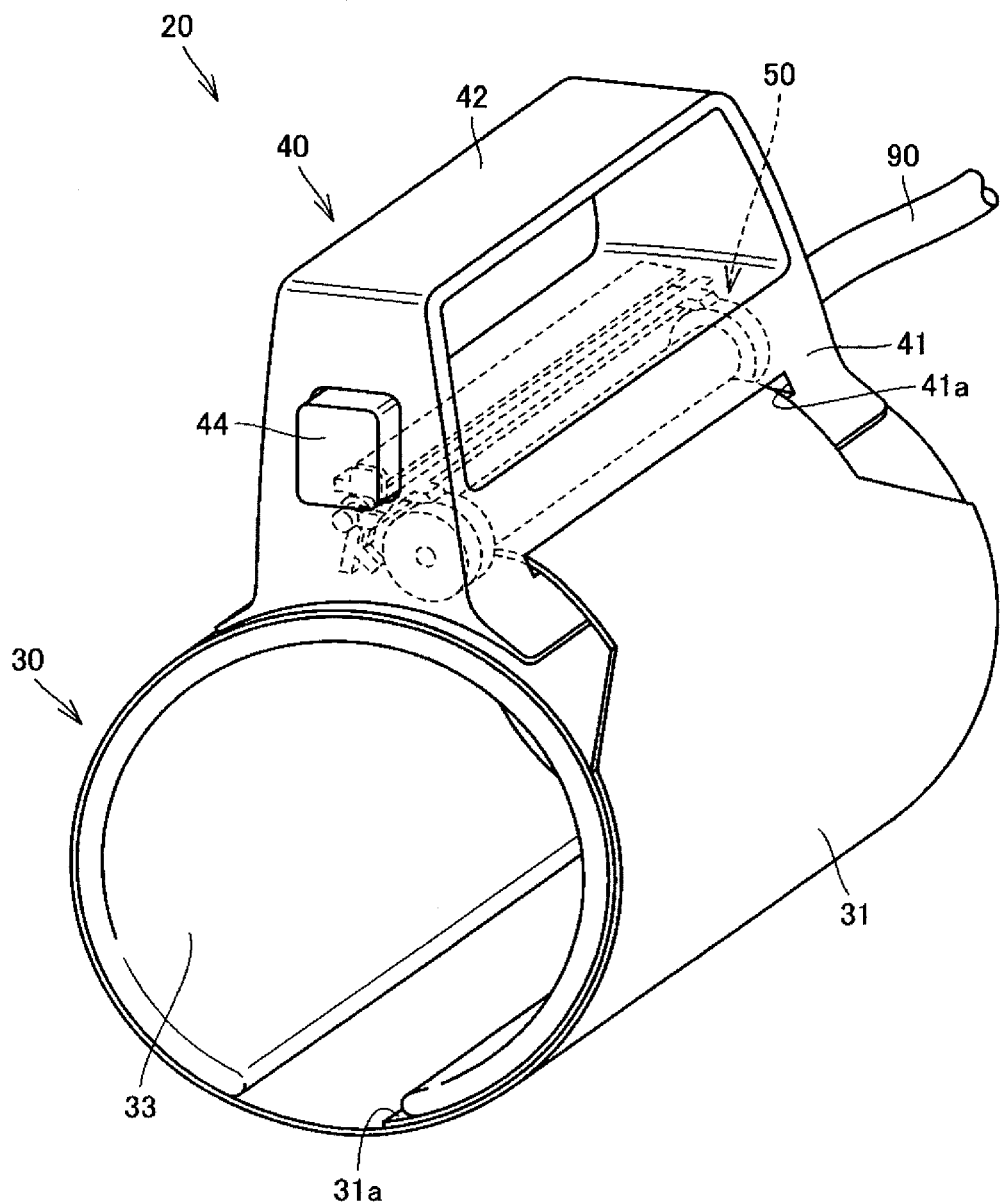
FIG. 4 is a perspective view showing a state that a cuff main body portion of a sphygmomanometer cuff in an embodiment of the present invention has a reduced diameter.
Figure 5:
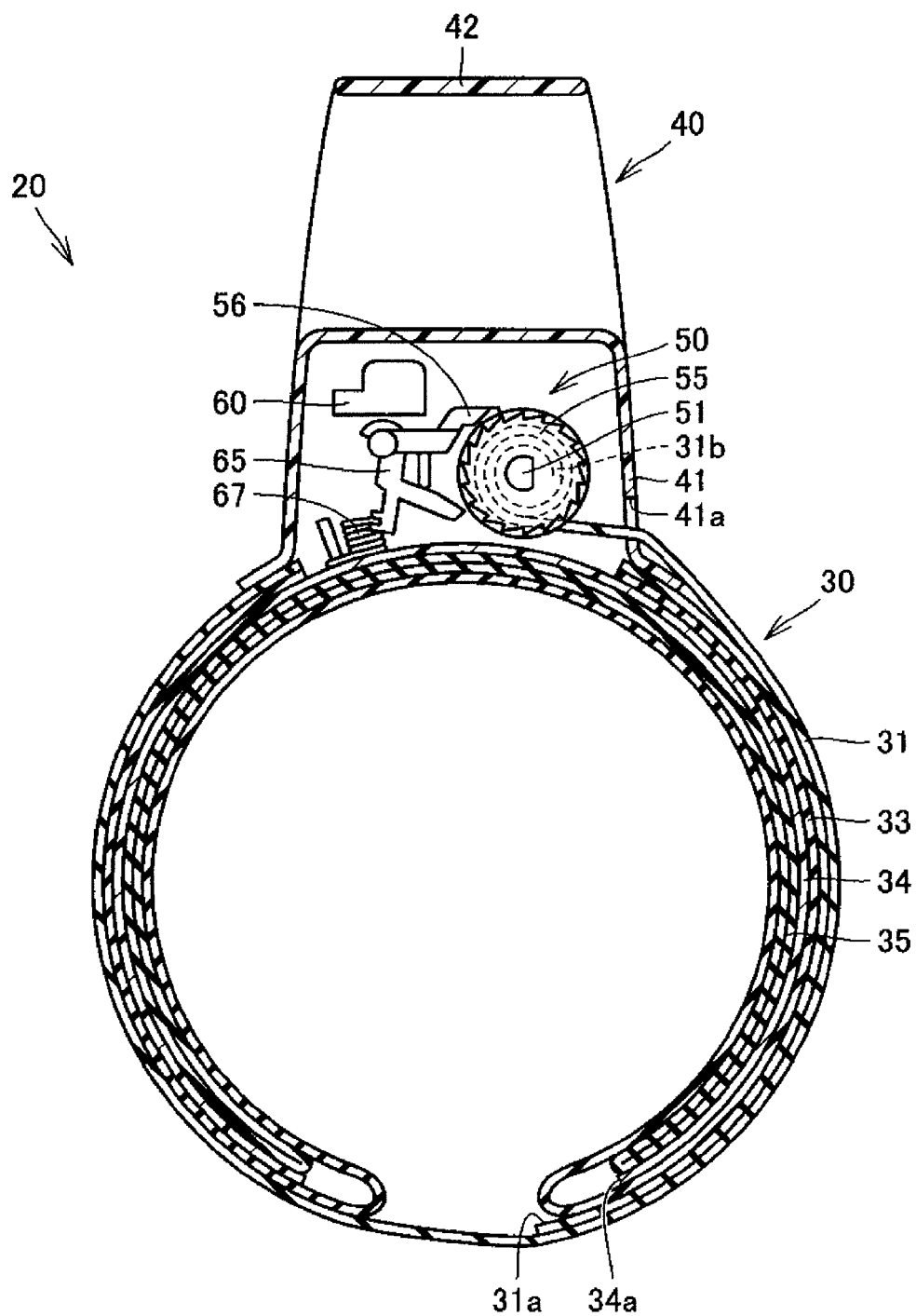
FIG. 5 is a sectional view showing the state that the cuff main body portion of the sphygmomanometer cuff in an embodiment of the present invention has the reduced diameter.
Figure 6:
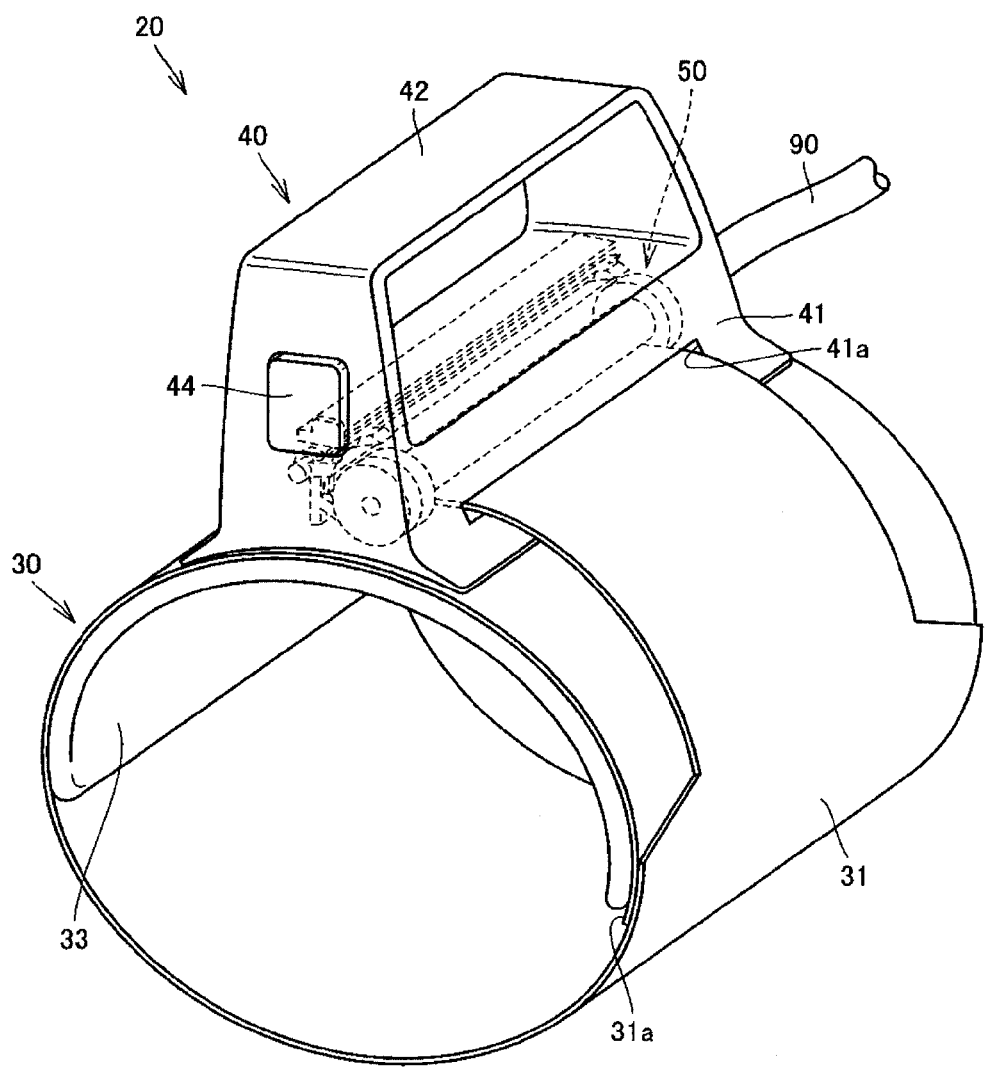
FIG. 6 is a perspective view showing a state that the cuff main body portion of the sphygmomanometer cuff in an embodiment of the present invention has an extended diameter.
Figure 7:
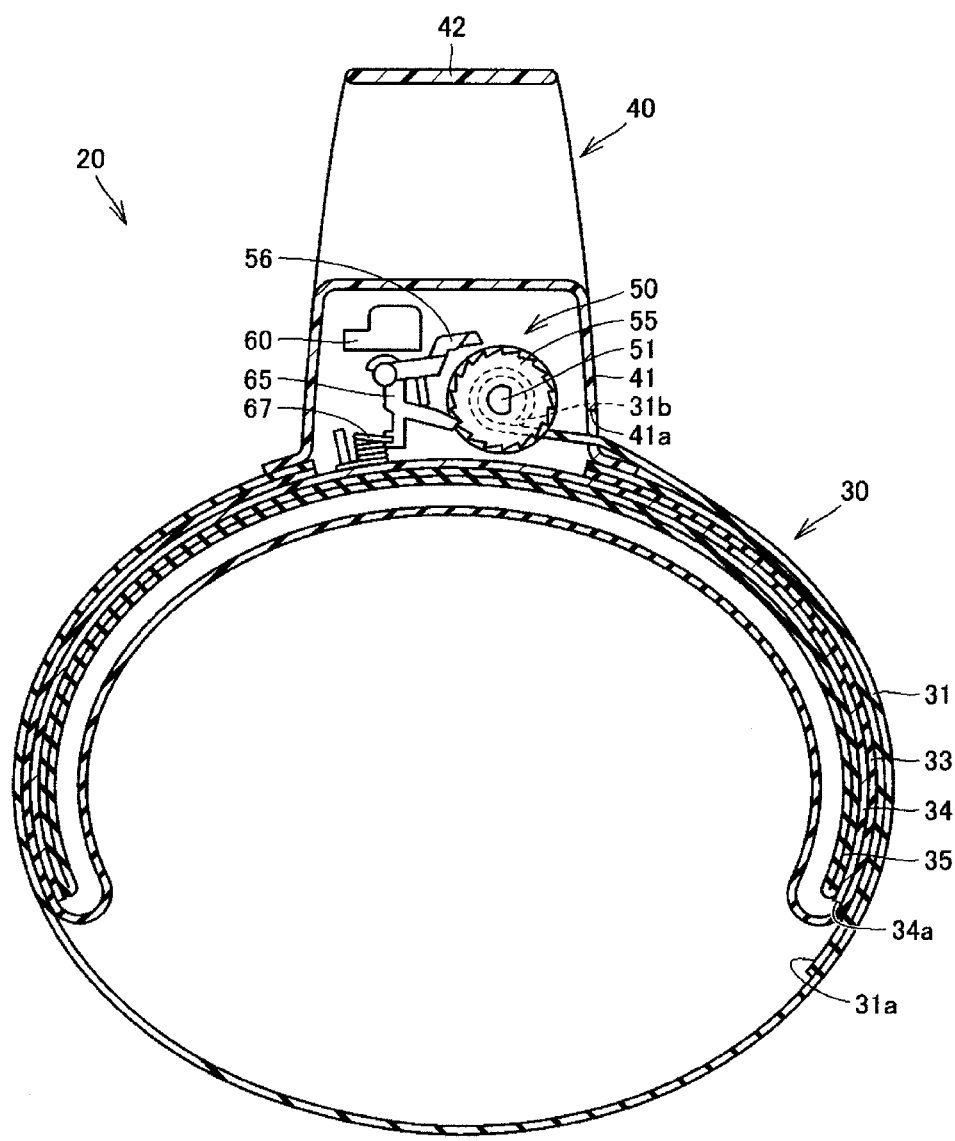
FIG. 7 is a sectional view showing the state that the cuff main body portion of the sphygmomanometer cuff in an embodiment of the present invention has the extended diameter.
Figure 8:
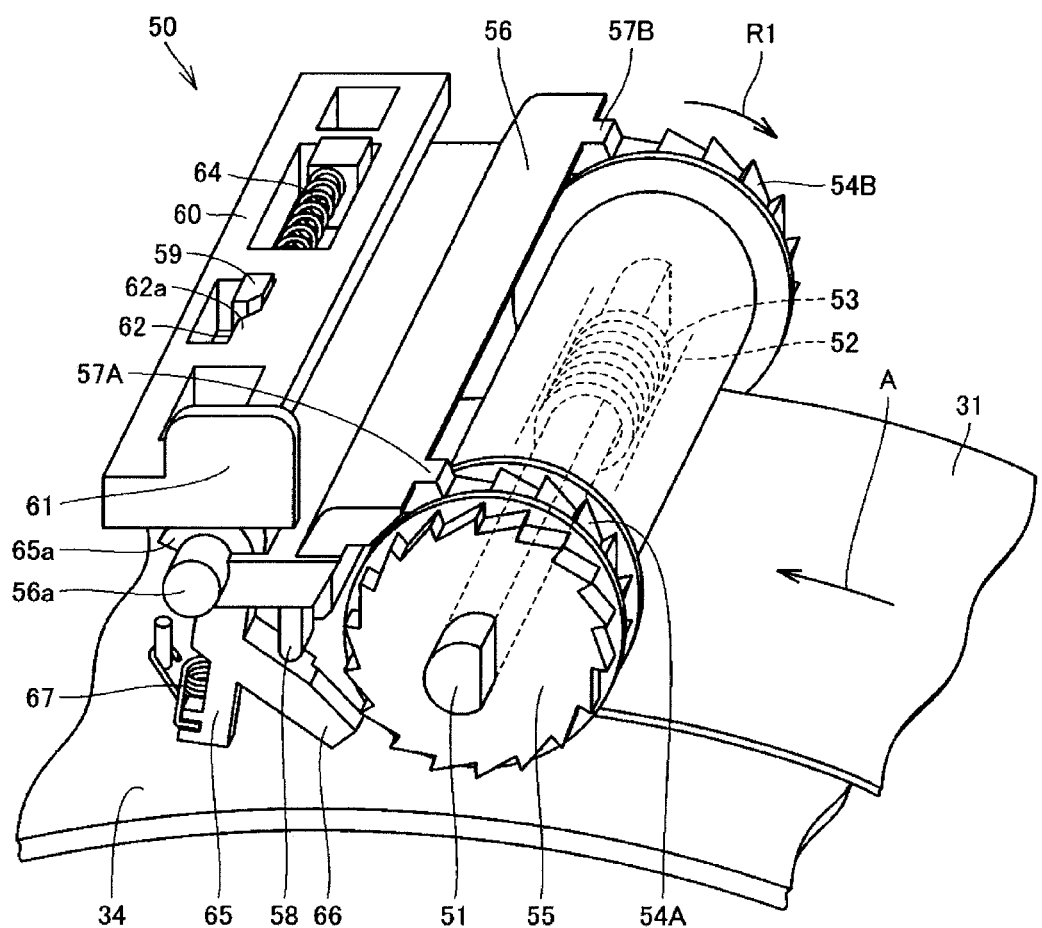
FIG. 8 is a schematic perspective view showing a state that a wrapping length adjustment mechanism of the sphygmomanometer cuff in an embodiment of the present invention performs a diameter reducing action.
Figure 9:
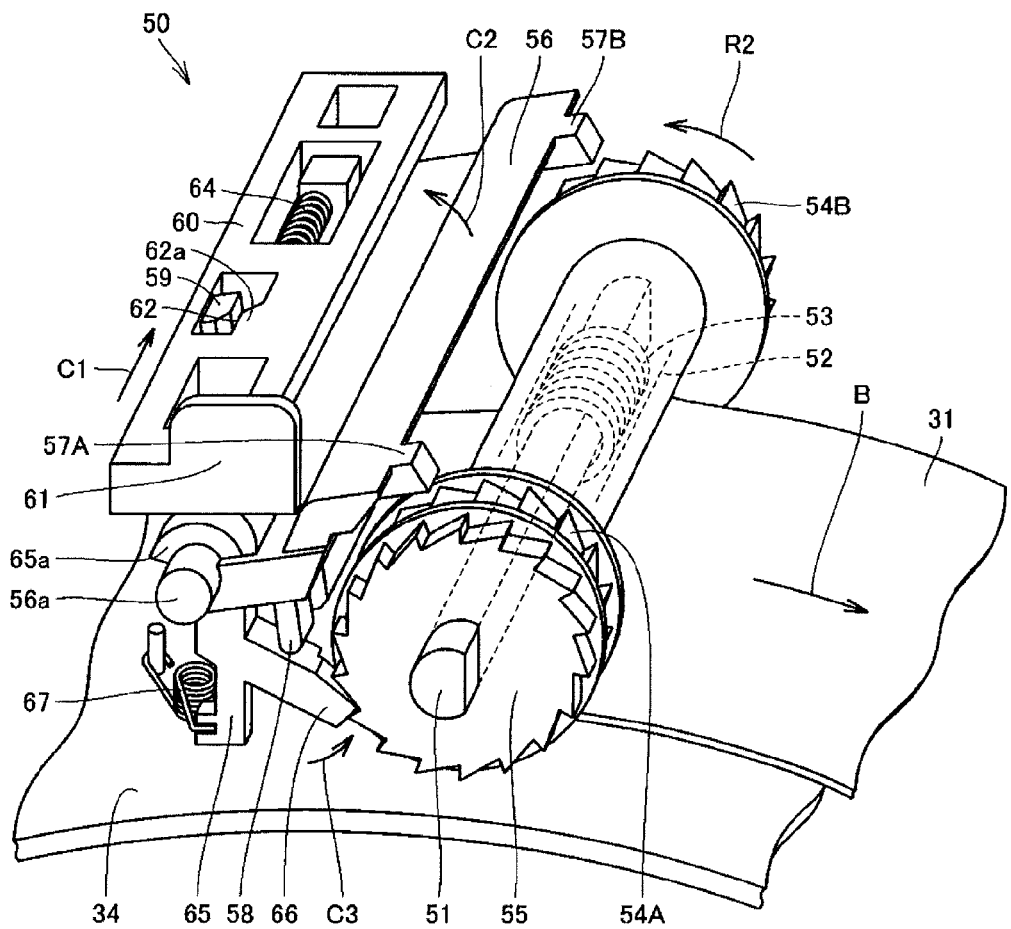
FIG. 9 is a schematic perspective view in a case where the wrapping length adjustment mechanism of the sphygmomanometer cuff in an embodiment of the present invention is in a diameter-extendable state.

FIGS. 4 to 7 are views showing detailed structures of the sphygmomanometer cuff in the embodiment of the present invention. FIGS. 4 and 5 are a perspective view and a sectional view showing a state that the cuff main body portion has a reduced diameter. FIGS. 6 and 7 are a perspective view and a sectional view showing a state that the cuff main body portion has an extended diameter. FIGS. 8 and 9 are views for illustrating a configuration of a wrapping length adjustment mechanism provided in the sphygmomanometer cuff in the embodiment of the present invention, and an action thereof. FIG. 8 is a schematic perspective view showing a state that the wrapping length adjustment mechanism performs a diameter reducing action. FIG. 9 is a schematic perspective view in a case where the wrapping length adjustment mechanism is in a diameter-extendable state. Next, a configuration and actions of the sphygmomanometer cuff in the present embodiment will be described in detail with reference to FIGS. 4 to 9.

As shown in FIGS. 4 to 7, the cuff 20 in the present embodiment has the tubular cuff main body portion 30 to be attached to the upper arm, and the gripping portion 40 provided on the outer peripheral surface of the cuff main body portion 30. The gripping portion 40 includes a base portion 41 serving as a part to be attached to the cuff main body portion 30, and a grip 42 serving as a part to be held by a hand during attachment. The cuff main body portion 30 is formed into a tubular shape into which the upper arm is insertable from the axial direction. The gripping portion 40 is fixed to the cuff main body portion 30 so that the grip 42 extends in the parallel direction to the axial direction of the tubular cuff main body portion 30. A wrapping length adjustment mechanism 50 is arranged at a position on the outer peripheral surface of the cuff main body portion 30 inside the base portion 41 of the gripping portion 40. An insertion port 41a into which a tightening belt 31 described later is inserted is provided at a predetermined position on a side surface of the base portion 41. A push button 44 serving as a switching portion described later is provided at a predetermined position on an outer surface of the gripping portion 40.

The cuff main body portion 30 is mainly provided with the tightening belt 31 annularly wrapped around, an outer package cover 33, a curler 34 serving as a curved elastic plate, and the air bladder 35. The outer package cover 33 is attached at a predetermined position on an inner peripheral surface of the tightening belt 31. The curler 34 and the air bladder 35 are accommodated in the outer package cover 33. It should be noted that the above gripping portion 40 is attached at a predetermined position on an outer peripheral surface of the outer package cover 33.

The tightening belt 31 is formed by a band-shaped member made of a cloth or the like substantially having no stretchability in the circumferential direction, and has one end 31a and the other end 31b in the circumferential direction. A part of the tightening belt 31 close to the other end 31b overlies the outer peripheral side of a part of the tightening belt 31 close to the one end 31a. Further, the other end 31b of the tightening belt 31 is accommodated in the base portion 41 of the gripping portion 40 via the insertion port 41a provided in the above gripping portion 40, and fixed to a winding roller 52 arranged in the base portion 41 (see FIGS. 8 and 9). Thereby, the cuff main body portion 30 is formed into an annular form having the hollow opening portion into which the upper arm is insertable from the axial direction thereof.

Circumferential length of the tightening belt 31 is variably adjusted by the wrapping length adjustment mechanism 50 provided in the above gripping portion 40. In a state that the circumferential length of the tightening belt 31 is shortened as shown in FIGS. 4 and 5, the cuff main body portion 30 is in a reduced diameter state (a state that a diameter is reduced). In a state that the circumferential length of the tightening belt 31 is extended as shown in FIGS. 6 and 7, the cuff main body portion 30 is in an extended diameter state (a state that the diameter is extended).

The outer package cover 33 is formed, for example, by a member such as a cloth made of a low friction member having stretchability, and attached onto the inner peripheral surface of the above tightening belt 31. More specifically, the outer peripheral surface of the outer package cover 33 is joined to the inner peripheral surface of the tightening belt 31 by adhesion, welding or the like, so that the outer package cover 33 is fixed to the tightening belt 31.

The curler 34 accommodated in the outer package cover 33 is made of a flexible member formed by injection molding a resin material such as polypropylene as a base material. More specifically, the curler 34 is formed by an annular curved elastic plate having a cut 34a along the axial direction at a predetermined position in the circumferential direction, and formed in a C shape or a U shape when the curler is cut along a plane orthogonal to the axial direction. The curler 34 maintains its own annular form and is formed to be elastically deformable in the radial direction. Therefore, the curler 34 has a largely extended diameter in the above extended diameter state, and on the other hand, has a narrowed diameter in the above reduced diameter state. It should be noted that in a case where the cuff main body portion 30 is in the extended diameter state, the cuff main body portion 30 is largely extended by an elastic force of the curler 34. Thus, the upper arm is easily put in and drawn out the inside of the hollow opening portion of the cuff main body portion 30.

The air bladder 35 is a bag shape member capable of being expanded and contracted and is formed, for example, by overlapping two resin films and welding peripheral edges thereof. The inner cavity of the air bladder 35 is connected to the air tube 90 via a nipple (not shown). The inner cavity of the air bladder 35 is pressurized and depressurized by the pressurization pump 71 and the exhaust valve 72 provided in the main body 10 at the time of the measurement, and thereby, the air bladder 35 is expanded or contracted.

As shown in FIGS. 8 and 9, the wrapping length adjustment mechanism 50 is mainly provided with a shaft 51, the winding roller 52, a first stopper 56, a slider 60, and a second stopper 65. The wrapping length adjustment mechanism 50 including these constituent elements is arranged on an outer peripheral surface of the curler 34 of the cuff main body portion 30 and in the base portion 41 of the gripping portion 40 as described above. The wrapping length adjustment mechanism 50 variably adjusts a wrapping length of the above tightening belt 31.

The shaft 51 is axially and rotatably supported on an axial support portion (not shown) and arranged so that the axial direction thereof matches with the axial direction of the cuff main body portion 30. A bias spring 53 serving as a bias portion is fitted onto the shaft 51. The bias spring 53 is formed by a coil spring, one end thereof is fixed to the base portion 41 of the gripping portion 40, and the other end thereof is fixed to the shaft 51. Further, the winding roller 52 is further fitted and fixed onto the shaft 51 onto which the bias spring 53 is fitted. The winding roller 52 is formed by a tubular member, and the other end 31b of the above tightening belt 31 (see FIGS. 5 and 7) is fixed at a predetermined position thereof.

First clutch plates 54A, 54B are arranged on the outer side in both ends of the winding roller 52 in the axial direction. The first clutch plates 54A, 54B are both fixed to the shaft 51. The first clutch plates 54A, 54B are formed by disc shape members, and wedge shape teeth are continuously provided on outer peripheral surfaces thereof along the circumferential direction. A second clutch plate 55 is arranged on the further outer side of the first clutch plate 54A. The second clutch plate 55 is also fixed to the shaft 51. The second clutch plate 55 is also formed by a disc shape member, and wedge shape teeth are continuously provided on an outer peripheral surface thereof along the circumferential direction. It should be noted that the first clutch plates 54A, 54B and the second clutch plate 55 are formed so that the forward directions of the wedge shape teeth are opposite to each other in the circumferential direction of the shaft 51.

As described above, the winding roller 52, the first clutch plates 54A, 54B and the second clutch plate 55 fixed to the shaft 51 are all driven and rotated following rotation of the shaft 51. The above bias spring 53 is built into the winding roller 52 in a compressed state so that the tightening belt 31 is always biased in the direction in which the tightening belt is wound by the winding roller 52. As a result, bias force of the bias spring 53 always acts on the tightening belt 31 in the direction in which the wrapping length thereof is shortened.

Meanwhile, the first stopper 56 is arranged on the side of the above winding roller 52, and has a rotation shaft portion 56a extending in the direction matched with the axial direction of the cuff main body portion 30. The rotation shaft portion 56a of the first stopper 56 is axially and rotatably supported on an axial support portion (not shown). Thereby, the first stopper 56 is rotatable around the rotation shaft portion 56a. First clutch claws 57A, 57B capable of being meshed with the teeth provided in the above first clutch plates 54A, 54B are provided at predetermined positions of the first stopper 56. The first clutch claws 57A, 57B are meshed with the teeth of the above first clutch plates 54A, 54B so as to restrict rotation of the first clutch plates 54A, 54B in the predetermined direction. It should be noted that the first stopper is always biased toward the side of the winding roller 52 by a spring (not shown).

The first stopper 56 further has an engagement portion 58 and an engagement projection portion 59. The engagement portion 58 is formed by a pin shape part provided so as to protrude downward from a predetermined position on a lower surface of the first stopper 56, and pushes down the second stopper 65 described later. The engagement projection portion 59 is formed by a columnar part provided so as to protrude upward from a predetermined position on an upper surface of the first stopper 56, and engaged with the slider 60 described later.

The slider 60 is arranged on the upper side of the first stopper 56, and formed slidably movably in the direction along the axial direction of the cuff main body portion 30. An engagement hole portion 62 to be engaged with the engagement projection portion 59 of the above first stopper 56 is provided at a predetermined position of the slider 60. A stepped portion 62a onto which the engagement projection portion 59 can be placed is provided on a side surface of the engagement hole portion 62. The slider 60 also has an abutment surface 61 to be abutted with the push button 44 provided in the above gripping portion 40 in one end thereof in the longitudinal direction. It should be noted that a spring 64 is attached to the slider 60, so that the slider 60 is always biased toward the side where the push button 44 is positioned by the bias force of the spring 64.

The second stopper 65 is arranged on the lower side of the first stopper and on the side of the above second clutch plate 55. The second stopper 65 has a hanging portion 65a for hanging the rotation shaft portion 56a of the first stopper 56, and a second clutch claw 66 capable of being meshed with the teeth provided in the above second clutch plate 55. The hanging portion 65a is a part for rotating the second stopper 65 around the rotation shaft portion 56a of the first stopper 56. The second clutch claw 66 is meshed with the teeth of the above second clutch plate 55 so as to restrict rotation of the second clutch plate 55 in the predetermined direction. It should be noted that a spring 67 is attached to the second stopper 65, so that the second stopper 65 is always biased in the predetermined direction by the bias force of the spring 67.

In the wrapping length adjustment mechanism 50 described above, the first clutch plates 54A, 54B fixed to the shaft 51 and the first clutch claws 57A, 57B provided in the first stopper 56 form a one-way clutch serving as a first restriction portion, and the second clutch plate 55 fixed to the shaft 51 and the second clutch claw 66 provided in the second stopper 65 form a one-way clutch serving as a second restriction portion.

The one-way clutch serving as the first restriction portion restricts the rotation direction of the shaft 51 to only one particular direction (hereinafter, referred to as the first direction) in a state that the first clutch claws 57A, 57B are respectively meshed with the first clutch plates 54A, 54B, and does not restrict the rotation of the shaft 51 in a non-meshing state. Meanwhile, the one-way clutch serving as the second restriction portion restricts the rotation direction of the shaft 51 to only one particular direction (hereinafter, referred to as the second direction) in a state that the second clutch claw 66 is meshed with the second clutch plate 55, and does not restrict the rotation direction of the shaft 51 in a non-meshing state. The rotation direction of the shaft 51 restricted by the one-way clutch serving as the first restriction portion and the rotation direction of the shaft 51 restricted by the one-way clutch serving as the second restriction portion are in opposite directions to each other. Thus, the above first direction and the second direction are also in opposite directions to each other.

In the above wrapping length adjustment mechanism 50, the one-way clutch serving as the first restriction portion and the one-way clutch serving as the second restriction portion are not in a meshing state at the same time, and only one of the one-way clutches is always in the meshing state. A state where the one-way clutch serving as the first restriction portion is in the meshing state and the one-way clutch serving as the second restriction portion is in the non-meshing state is called a "first state," and a state where the one-way clutch serving as the second restriction portion is in the meshing state and the one-way clutch serving as the first restriction portion is in the non-meshing state is called a "second state." The "first state" and the "second state" are switched in conjunction with an action of the push button 44, serving as the switching portion provided in the above gripping portion 40. Hereinafter, a mechanism thereof will be described in detail.

FIG. 8 shows a state of the wrapping length adjustment mechanism 50 in the above first state. In the first state shown in FIG. 8, the push button 44 serving as the switching portion is not pressed down, and the slider 60 is biased by the spring 64 and positioned on the side of the push button 44. In this state, the engagement projection portion 59 of the first stopper 56 engaged with the engagement hole portion 62 of the slider 60 is not placed onto the stepped portion 62*a*. Thus, the first stopper 56 is biased by the spring (not shown), and the first clutch claws 57A, 57B are meshed with the teeth of the first clutch plates 54A, 54B. In the above state, the second stopper 65 is pushed down against the bias force of the spring 67 by the engagement portion 58 provided in the first stopper 56, and the second clutch claw 66 is not meshed with the teeth of the second clutch plate 55. In the above state, the winding roller 52 is rotated in an arrow R1 direction in the figure by the bias force of the bias spring 53, and the tightening belt 31 is biased and wound in an arrow A direction in the figure. Therefore, the tightening belt 31 is variably adjusted only in the direction in which the wrapping length thereof is shortened.

FIG. 9 shows a state of the wrapping length adjustment mechanism 50 in the above second state. In the second state shown in FIG. 9, the push button 44 serving as the switching portion is pressed down, and the slider 60 is pushed down in an arrow C1 direction in the figure against the bias force of the spring 64. In this state, the engagement projection portion 59 of the first stopper 56 engaged with the engagement hole portion 62 of the slider 60 is placed onto the stepped portion 62*a*. Thus, the first stopper is rotated in an arrow C2 direction in the figure against the bias force of the spring (not shown), and the meshing state of the first clutch claws 57A, 57B with the teeth of the first clutch plates 54A, 54B is released. In the above state, the push-down of the second stopper 65 is released by the engagement portion 58 provided in the first stopper 56, the second stopper 65 is rotated in an arrow C3 direction in the figure by the bias force of the spring 67, and the second clutch claw 66 is meshed with the teeth of the second clutch plate 55. In the above state, the rotation of the winding roller 52 is prevented against the bias force of the bias spring 53. Only in a case where force is applied in the direction in which the tightening belt 31 is pulled out from the winding roller 52, the winding roller 52 is rotated in an arrow R2 direction in the figure, so that the tightening belt 31 can be pulled out in an arrow B direction in the figure. Therefore, the tightening belt 31 is variably adjustable only in the direction in which the wrapping length thereof is extended.

As described above, in the cuff 20 in the present embodiment, by operating the push button 44 serving as the switching portion, the above first state where the wrapping length of the tightening belt 31 is variably adjusted only in the direction in which the wrapping length of the tightening belt 31 is shortened, and the second state where the wrapping length of the tightening belt 31 is variably adjusted only in the direction in which the wrapping length of the tightening belt 31 is extended can be switched. Therefore, attachment procedures shown below can be realized.

Figure 10:
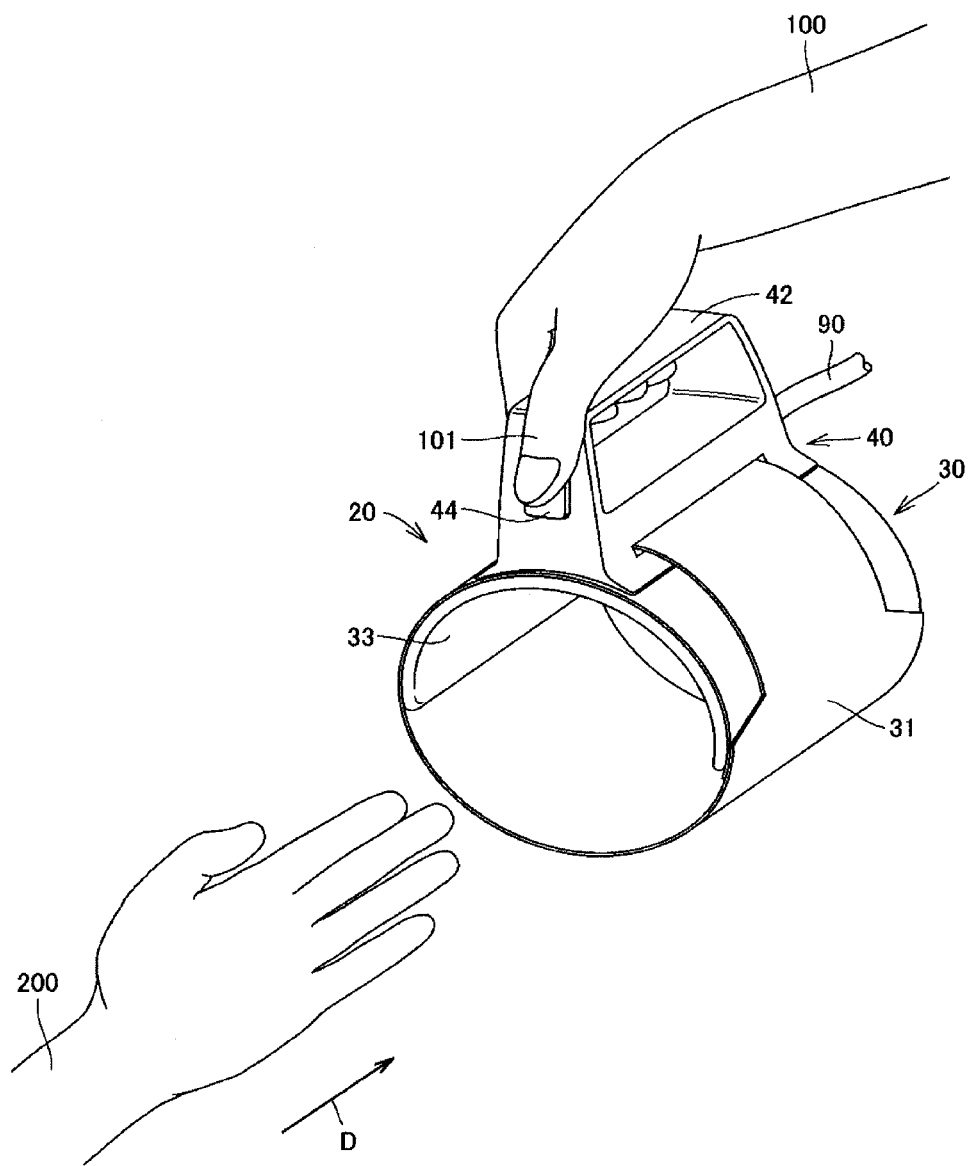
FIG. 10 is a view for illustrating attachment procedures of the sphygmomanometer cuff in an embodiment of the present invention.
Figure 11:
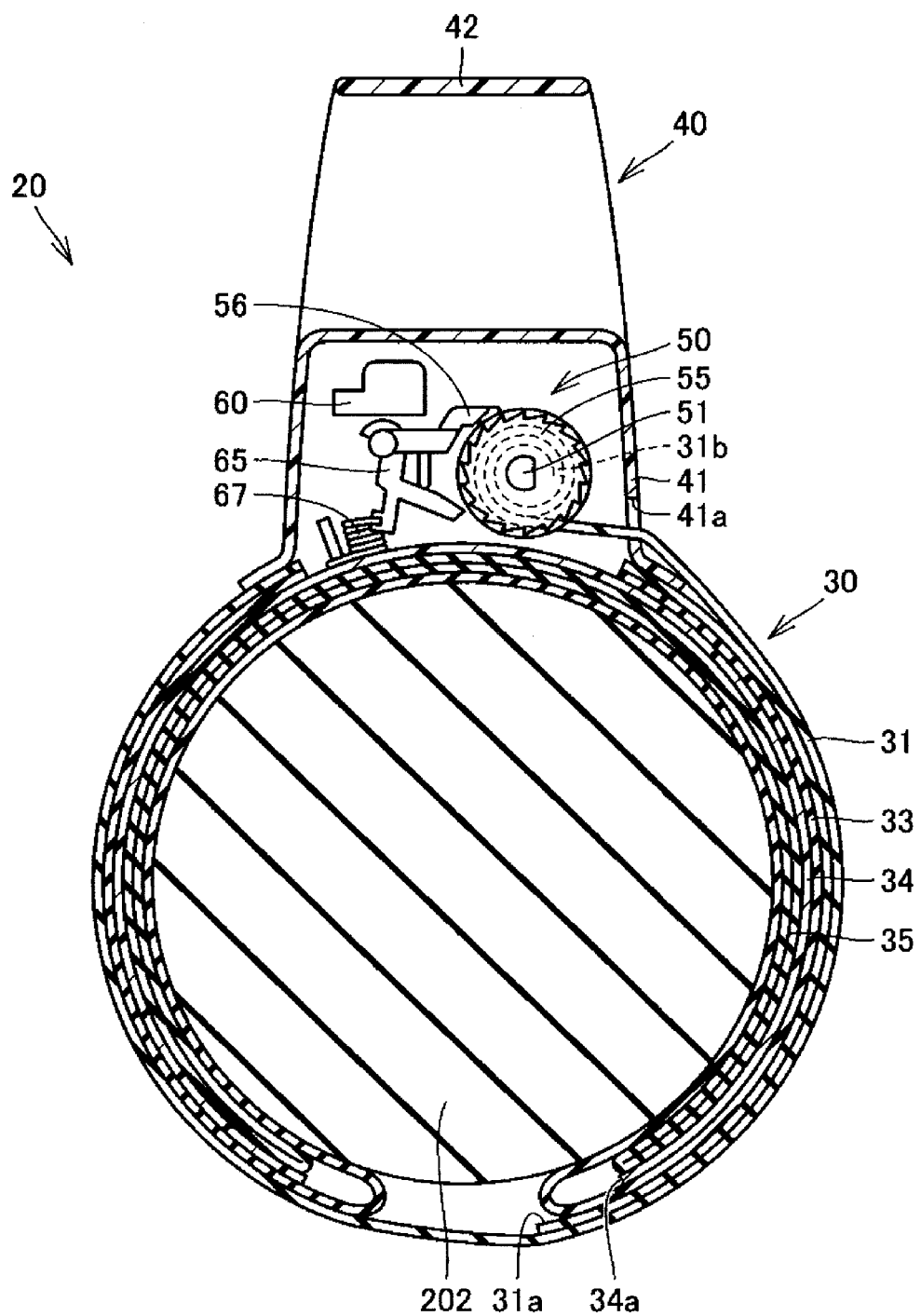
FIG. 11 is a schematic sectional view showing a state that the sphygmomanometer cuff in an embodiment of the present invention is attached to an upper arm.

FIG. 10 is a view for illustrating the attachment procedures of the sphygmomanometer cuff in the present embodiment. FIG. 11 is a schematic sectional view showing a state that the sphygmomanometer cuff in the present embodiment is attached to the upper arm. Next, the attachment procedures of the sphygmomanometer cuff in the present embodiment and a state after the attachment will be described with reference to FIGS. 10 and 11. It should be noted that FIG. 10 assumes a case where the cuff 20 is attached to an upper arm of a left arm.

As shown in FIG. 10, in time of attaching the cuff 20, the grip 42 of the cuff 20 is firstly held by a right hand 100, and the push button 44 is pressed down by a thumb 101 in this state. While maintaining the press-down state of the push button 44, the tightening belt 31 is pulled out from the insertion port 41*a* by a left hand, so that the cuff 20 is in the extended diameter state. It should be noted that since the wrapping length adjustment mechanism 50 is in the above second state in this state, the wrapping length of the tightening belt 31 is extended by an amount fed out from the winding roller 52, and the wrapping length is maintained.

Next, while maintaining the press-down state of the push button 44, the left hand 200 is inserted into the hollow opening portion of the cuff main body portion 30 in an arrow D direction in the figure. The cuff main body portion 30 is placed onto the upper arm of the left hand 200, and the press-down state of the push button 44 is released by separating the thumb 101 of the right hand 100 pressing down the push button 44 from the push button 44. In this state, the wrapping length adjustment mechanism 50 is switched from the above second state to the first state. Thereby, the tightening belt 31 is wound by the winding roller 52 by operation of the bias spring 53, so that the wrapping length thereof is shortened. Thus, as shown in FIG. 11, the wrapping length of the tightening belt 31 is automatically adjusted only in the direction in which the wrapping length of the tightening belt 31 is shortened, so that the cuff main body portion 30 is wrapped around and attached to the upper arm 202 of the left hand 200 with proper tightening force.

It should be noted that in a case where the cuff 20 is detached from the upper arm 202 of the left hand 200 after the measurement of the blood pressure values, operation similar to the initial operation in time of attaching the above cuff 20 is performed. That is, the grip 42 of the cuff 20 is held by the right hand 100, the push button 44 is pressed down by the thumb 101 in this state, and then while maintaining the press-down state of the push button 44, the upper arm 202 and/or the right hand 100 is moved so that the upper arm 202 and the right hand 100 holding the grip 42 are brought apart from each other. Thereby, the tightening belt 31 is pulled out from the insertion port 41*a*, so that the cuff 20 is in the extended diameter state. At the time, when the press-down state of the push button 44 is maintained, the extended diameter state is maintained. Thus, by drawing out the left hand 200 from the cuff main body portion 30, the cuff 20 can be detached. It should be noted that when the press-down state of the push button 44 is released after detaching the cuff 20, the cuff 20 is in the reduced diameter state, so that the cuff 20 can be compacted.

In the sphygmomanometer cuff 20 in the present embodiment and the sphygmomanometer 1 provided with the same described above, by operating the various constituent elements forming the wrapping length adjustment mechanism 50 in conjunction with each other, the wrapping length of the tightening belt 31 is variably adjusted in conjunction with the press-down state of the push button 44. The push button 44 for switching the above first state and the second state is provided in the gripping portion 40 serving as a part to be held by the hand in time of the attachment. Thus, the holding of the grip 42 and the operation of the push button 44 can be performed at the same time by a hand which is different from the hand to which the cuff main body portion 30 is attached. Therefore, by adopting the above configuration, the sphygmomanometer cuff capable of attaching the cuff 20 to the upper arm with a single touch operation, and the sphygmomanometer provided with the same can be provided.

Since the cuff can be attached with the single touch operation, even elderly people, females, and the like having relatively inferior strength can easily attach the cuff. Thus, a sphygmomanometer cuff having highly excellent handling, and the sphygmomanometer provided with the same can be provided. Since the attachment is easily performed, the cuff main body portion 30 is positioned at a proper position of the upper arm and the cuff is relatively easily attached. Thus, generation of measurement errors due to attachment position displacement is reduced, so that precise blood pressure values can be measured. Further, since the air bladder 35 is pushed onto the upper arm by the curler 34 with proper pressing force at the time of the attachment, the precise blood pressure values can be measured with favorable reproducibility.

In the sphygmomanometer cuff 20 in the present embodiment and the sphygmomanometer 1 provided with the same, with sufficiently long length of the tightening belt 31, by pulling out a necessary amount of the tightening belt 31 from the winding roller 52 in the above second state, the wrapping length of the tightening belt 31 can be extended as required. Therefore, the sphygmomanometer cuff applicable to any subject ranging from a subject having long circumferential length of the upper arm to a subject having short circumferential length of the upper arm, and the sphygmomanometer provided with the same can be provided.

It should be noted that although a case where the switching portion is formed as the push button is shown as an example and described in the embodiment of the present invention described above, the switching portion can be formed as a sliding type button or a dial type button instead of the push button, or as a lever in place of the button. A case where the push button serving as the switching portion is provided at a position where the push button can be operated by the thumb of the gripping portion is shown as an example and described in the above embodiment of the present invention. However, the position where the switching portion is provided is not limited to this position but the switching portion may be provided at other positions of the gripping portion or may be provided in the cuff main body portion in the vicinity of the gripping portion. In any case, as long as the switching portion can be operated by the hand holding the gripping portion while the gripping portion is held, the switching portion may be provided at any position.

A case where the curler serving as the curved elastic plate is accommodated in the outer package cover is shown as an example and described in the above embodiment of the present invention. However, the curler is not necessarily provided, but only the air bladder can be accommodated in the outer package cover. A case where an embodiment of the present invention is applied to the sphygmomanometer of the upper arm type and the sphygmomanometer cuff provided in the same is shown as an example in the above embodiment of the present invention. However, as a matter of course, embodiments of the present invention are also applicable to a sphygmomanometer of a wrist type and a sphygmomanometer cuff provided in the same, a sphygmomanometer of an ankle type and a sphygmomanometer cuff provided in the same, and the like.

A case where an embodiment of the present invention is applied to the sphygmomanometer capable of measuring the systolic blood pressure value and the diastolic blood pressure value is shown as an example and described in the above embodiment of the present invention. However, embodiments of the present invention are also applicable to a blood pressure information measurement device capable of measuring blood pressure information other than the systolic blood pressure value and the diastolic blood pressure value (such as an average blood pressure value, the pulse wave, pulsation, and an AI (Augmentation Index) value).

As described above, the embodiments disclosed herein are illustrative in all aspects and should not be construed as being restrictive. The technical scope of the present invention is defined by the claims, and meanings equivalent to the claims and all modifications within the scope are intended to be encompassed herein.

DESCRIPTION OF SYMBOLS

1: Sphygmomanometer
10: Main body
11: Control unit
12: Memory unit
14: Display unit
16: Operation unit
18: Power supply unit
20: Cuff
30: Cuff main body portion
31: Tightening belt
31a: One end
31b: Other end
33: Outer package cover
34: Curler
34a: Cut
35: Air bladder
40: Gripping portion
41: Base portion
41a: Insertion port
42: Grip
44: Push button
50: Wrapping length adjustment mechanism
51: Shaft
52: Winding roller
53: Bias spring
54A, 54B: First clutch plate
55: Second clutch plate
56: First stopper
56a: Rotation shaft portion
57A, 57B: First clutch claw
58: Engagement portion
59: Engagement projection portion
60: Slider
61: Abutment surface
62: Engagement hole portion
62a: Stepped portion
64: Spring
65: Second stopper
65a: Hanging portion 66: Second clutch claw
67: Spring
70: Air system component
71: Pressurization pump
72: Exhaust valve
73: Pressure sensor
74: Pressurization pump drive circuit
75: Exhaust valve drive circuit
76: Oscillation circuit
90: Air tube
100: Right hand
101: Thumb
200: Left hand

The invention claimed is:

1. A cuff for a blood pressure information measurement device configured to be attached to a measurement site of a living body and used for measurement of blood pressure information, comprising:
   a cuff main body portion formed into an annular form into which the measurement site is insertable from an axial direction, and configured to be attached to the measurement site in time of the measurement; and
   a gripping portion provided on an outer peripheral surface of the cuff main body portion, wherein
   the cuff main body portion includes a fluid bag for compressing the living body, a tightening belt wrapped around an outer side of the fluid bag, and a wrapping length adjustment mechanism for variably adjusting a wrapping length of the tightening belt,
   the wrapping length adjustment mechanism has a winding roller for winding and feeding the tightening belt, a bias portion for pulling and biasing the tightening belt in a direction in which the wrapping length of the tightening belt is shortened, a first restriction portion for restricting extension of the wrapping length of the tightening belt, and a second restriction portion for restricting shortening of the wrapping length of the tightening belt, and
   each of the first restriction portion and the second restriction portion is formed by a one-way clutch additionally provided in the winding roller,
   the cuff further comprising a switching portion for selectively switching whether the wrapping length adjustment mechanism is in a first state where restriction by the second restriction portion is released, restriction by the first restriction portion is applied, and thereby, the wrapping length of the tightening belt is variably adjusted only in the direction in which the tightening belt is pulled by the bias portion and the wrapping length thereof is shortened, or in a second state where the restriction by the first restriction portion is released, the restriction by the second restriction portion is applied, and thereby, the wrapping length of the tightening belt is variably adjustable only in a direction in which the wrapping length of the tightening belt is extended, the switching portion being provided in the gripping portion or the cuff main body portion in a vicinity of the gripping portion.

2. The cuff for the blood pressure information measurement device according to claim 1, wherein the switching portion is formed by a push button.

3. The cuff for the blood pressure information measurement device according to claim 2, wherein the wrapping length adjustment mechanism is in the second state in conjunction with a press-down state of the push button, and in the first state in conjunction with release of the press-down state of the push button.

4. The cuff for the blood pressure information measurement device according to claim 1, wherein the bias portion is formed by a spring attached to the winding roller.

5. The cuff for the blood pressure information measurement device according to claim 1, further comprising a flexible curved elastic plate elastically deformable in a radial direction of the cuff main body portion on the outer side of the fluid bag and on an inner side of the tightening belt.

6. A blood pressure information measurement device, comprising:
   a cuff for a blood pressure information measurement device according to claim 1;
   expanding/contracting mechanisms for expanding and contracting a fluid bag; and
   a blood pressure information acquiring unit for acquiring blood pressure information.

* * * * *